(12) United States Patent
Kraft

(10) Patent No.: US 9,517,992 B2
(45) Date of Patent: Dec. 13, 2016

(54) ORGANIC COMPOUNDS

(71) Applicant: Givaudan, S.A., Vernier (CH)

(72) Inventor: Philip Kraft, Duebendorf (CH)

(73) Assignee: Givaudan S.A., Vernier (CH)

( * ) Notice: Subject to any disclaimer, the term of this patent is extended or adjusted under 35 U.S.C. 154(b) by 59 days.

(21) Appl. No.: 14/398,064

(22) PCT Filed: Mar. 15, 2013

(86) PCT No.: PCT/EP2013/055364
§ 371 (c)(1),
(2) Date: Oct. 30, 2014

(87) PCT Pub. No.: WO2013/170976
PCT Pub. Date: Nov. 21, 2013

(65) Prior Publication Data
US 2015/0111811 A1   Apr. 23, 2015

(30) Foreign Application Priority Data

May 16, 2012  (GB) .................................. 1208566.8

(51) Int. Cl.
| | | |
|---|---|---|
| *C07C 49/203* | (2006.01) | |
| *C07C 49/04* | (2006.01) | |
| *C11B 9/00* | (2006.01) | |

(52) U.S. Cl.
CPC ............. *C07C 49/203* (2013.01); *C07C 49/04* (2013.01); *C11B 9/0015* (2013.01)

(58) Field of Classification Search
CPC ....... C07C 49/04; C07C 49/203; C11B 9/0015
See application file for complete search history.

(56) References Cited

U.S. PATENT DOCUMENTS

2002/0176838 A1* 11/2002 Kraft .................. A23L 1/22628
424/76.1
2006/0014984 A1   1/2006  Dobler et al.

OTHER PUBLICATIONS

Kraft, et al. "Musk or Violet? Design, synthesis and odor of seco-derivatives of a musky carotol lead", Tetrahederon, vol. 62, (2006), pp. 12211-12219.*
PCT/EP2013/055364—International Search Report, mailed Jun. 5, 2013.
PCT/EP2013/055364—International Written Opinion, mailed Jun. 5, 2013.
PCT/EP2013/055364—International Preliminary Report on Patentability, issued Nov. 18, 2014.
GB 1208566.8—Great Britain Search Report, Sep. 13, 2012.
Kraft, et al., "Musk or Violet? Design, Synthesis and Odor of Seco-Derivates of a Musky Carotol Lead", Science Direct, Nov. 3, 2006, pp. 12211-12219, vol. 62, No. 52, Tetrahedron, Elsevier Science Publishers, Amsterdam, NL.

* cited by examiner

*Primary Examiner* — Ling Choi
*Assistant Examiner* — Lanee Reuther
(74) *Attorney, Agent, or Firm* — Curatolo Sidoti Co., LPA; Joseph G. Curatolo; Salvatore A. Sidoti

(57) ABSTRACT

Branched optionally unsaturated ketones particularly useful in providing typical and characteristic orris facets to perfume compositions.

9 Claims, No Drawings

ORGANIC COMPOUNDS

CROSS REFERENCE TO RELATED APPLICATIONS

This application is a national stage application of International Application No. PCT/EP2013/055364, filed 15 Mar. 2013, which claims priority from Great Britain Patent Application No. 1208566.8, filed 16 May 2012, from which applications priority is claimed, and which are incorporated herein by reference.

The present invention relates to novel compounds possessing olfactory properties reminiscent of orris oil. The invention furthermore refers to a method for their production, and to flavour and fragrance compositions containing these.

With a price of well above US$75,000, orris absolute constitutes probably the most expensive perfumery raw material still in use. Irones, α-irone (A), β-irone (B), and γ-irone (B) as depicted below, are the major constituents of orris oil and determine its typical odour, albeit there is some controversy about which irone stereoisomers do most. In any case, however, a stereoselective synthesis of any specific irone isomer would even be far more expensive than the natural material, and thus uneconomical as replacement. Some alpha-irone mixtures are available on the marker for about US$ 200, but albeit they elicit some of the desirable orris facets, no perfumery material so far can adequately replace orris absolute in perfumery at an affordable cost, available on an industrially practical synthetic route.

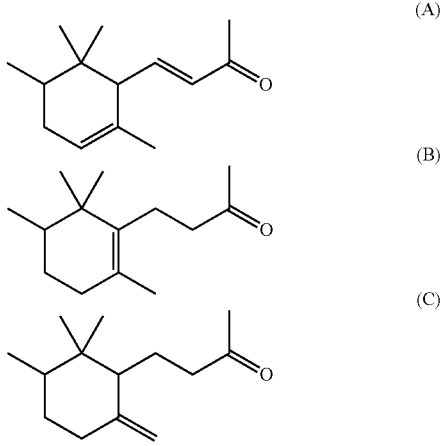

We have now found a small class of substituted branched ketones of formula (I) as defined herein below that possess typical, very natural orris-like odour. These novel compounds of formula (I) are structurally unrelated to the important irones which constitute the principle odorants of orris oil.

In a first embodiment, there is provided the use as fragrance of a compound of formula (I)

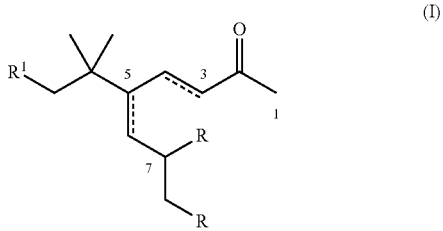

wherein
R and $R^1$ are independently selected from hydrogen and methyl;
the bond between C-3 and C-4 and the bond between C-5 and C-6 are single bonds; or
the dotted line together with the bond between C-3 and C-4 and the bond between C-5 and C-6 represent double bonds.

The compounds of this invention can be used as double-bond isomers as well as stereoisomeric mixtures that may be resolved in geometrically and/or enantiomerically pure form. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e.g. by stereoselective synthesis or by preparative HPLC and GC. Concerning the double bond isomerism, the (E)-configuration is preferred in both or either the C-3 and the C-5 double-bond position.

Non-limiting examples are compounds of formula (I) wherein R and $R^1$ are hydrogen.

Further non-limiting examples are compounds of formula (I) wherein $R^1$ is hydrogen and the dotted line together with the bond between C-3 and C-4 and between C-5 and C-6 represent double bonds. In one embodiment one or both double bonds are in (E)-configuration.

As specific examples of compounds of formula (I), one may cite, as non-limiting example, (3E,5E)-5-tert-butylocta-3,5-dien-2-one (R=$R^1$=H, $\Delta^{3,5}$), which possesses a typical orris, irone, sweet-violet odor with carrot-like and woody-leathery undertones. Apart from these very natural orris-like characteristic the compound is quite interesting since it possesses a far lower odour threshold, and a higher vapour pressure which results in a far more diffusive fragrant ingredient compared to the known irones.

Further non-limiting examples are compounds of formula (I) selected from the group consisting 5-tert-butylocta-3,5-dien-2-one (R=$R^1$=H, $\Delta^{3,5}$), 5-(tert-pentyl)octa-3,5-dien-2-one (R=H, $R^1$=Me, $\Delta^{2,5}$), 5-(tert-butyl)-7-methylnona-3,5-dien-2-one (R=Me, $R^1$=H, $\Delta^{2,5}$), 5-tert-butyloctan-2-one (R=$R^1$=H), 6,6-dimethyl-5-propyloctan-2-one (R=H, $R^1$=Me), and 5-tert-butyl-7-methylnonan-2-one (R=Me, $R^1$=H), both, their racemic mixtures, and the individually isolated isomers.

The compounds of formula (I) may be used alone, as mixtures thereof, or in combination with a base material. As used herein, the 'base material' includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, 'fragrance composition' means any composition comprising at least one compound of formula (I) and a base material, e.g. a diluent conventionally used in conjunction with odorants, such as dipropylene glycol (DPG), isopropyl myristate (IPM), triethyl citrate (TEC) and alcohol (e.g. ethanol).

The following list comprises examples of known odorant molecules, which may be combined with the compounds of formula (I) as herein defined:
essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. Azurone® [7-(3-methylbutyl)-1,5-benzodioxepin-3-one], anisaldehyde, α-amylcinnamaldehyde, Georgywood™, hydroxycitronellal, Iso E® Super, Isoraldeine®, Hedione®, Lilial®, maltol, methyl cedryl ketone, methylionone, verbenone, or vanillin;

ether and acetals, e.g. Ambrox®, geranyl methyl ether, rose oxide, or Spirambrene®;

esters and lactones, e.g. benzyl acetate, cedryl acetate, γ-decalactone, Helvetolide®, γ-undecalactone or vetivenyl acetate;

macrocycles, e.g. Ambrettolide, ethylene brassylate or Exaltolide®; and heterocycles, e.g. isobutylchinoline.

The compounds according to formula (I) may be used in a broad range of perfumed products, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.1 to 10 weight percent of the application. In one embodiment, compounds of the present invention may be employed in a fabric softener in an amount of from 0.001 to 0.1 weight percent. In another embodiment, compounds of the present invention may be used in fine perfumery in amounts from 0.01 to 20 weight percent (e.g. up to about 10 weight percent), more preferably between 0.01 and 5 weight percent. However, these values are given only by way of example, since the experienced perfumer may also achieve effects or may create novel accords with lower or higher concentrations.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a perfumed product, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odour notes of a consumer product base will be improved, enhanced, or modified.

Thus, the invention furthermore provides a method for improving, enhancing or modifying a consumer product base by means of the addition thereto of an olfactorily acceptable amount of at least one compound of formula (I).

The invention also provides a perfumed product comprising:
a) as odorant at least one compound of formula (I); and
b) a consumer product base.

As used herein, 'consumer product base' means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing crème. This list of products is given by way of illustration, and is not to be regarded as being in any way limiting.

To the best of our knowledge none of the compounds falling within the definition of formula (I) are described in the literature and are thus novel in their own right.

Accordingly, the present invention refers in a further aspect to compounds of formula (I)

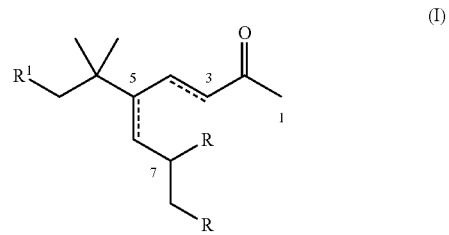

wherein
R and $R^1$ are independently selected from hydrogen and methyl;
the bond between C-3 and C-4 and the bond between C-5 and C-6 are single bonds; or
the dotted line together with the bond between C-3 and C-4 and the bond between C-5 and C-6 represent double bonds.

The compounds of formula (I) my be prepared starting with the addition of the Grignard reagent prepared from but-3-yn-2-ol with two equivalents of ethylmagnesium chloride to a corresponding ketone, or in sterically hindered cases in a two-step manner by first adding acetylene magnesium bromide, transforming the resulting product to a Grignard reagent itself, and making the latter react with acetaldehyde. The necessary ketone starting materials may be synthesized by a copper-catalyzed Grignard reaction with the corresponding acid chloride, or by applying a manganese-catalyzed acylation reaction. The secondary hydroxy function of the resulting alk-3-yne-2,5-diol derivatives of these ketones is then for instance oxidized with manganese dioxide, while the tertiary hydroxy function is eliminated. The elimination method influences the doubly-bond geometry, as would an inversion of the elimination-oxidation sequence. For the preferred (5E)-configuration it is advantageous to oxidize prior to elimination. Compounds of formula (I) wherein the bond between C-3 and C-4 represent double bond in (E)-configuration may be obtained by reducing both triple bond and carbonyl function with lithium aluminium hydride. Oxidation of the resulting allylic secondary alcohols with, for instance, manganese dioxide provides the double-unsaturated target structures of the general formula (I), which can then be hydrogenated, to provide the further derivatives of the formula (I).

The invention is now further described with reference to the following non-limiting examples. These examples are for the purpose of illustration only, and it is understood that variations and modifications can be made by one skilled in the art.

EXAMPLE 1

(3E,5E)-5-tert-Butylocta-3,5-dien-2-one
($R=R^1=H$, $\Delta^{3,5}$)

A solution of cerium trichloride (29.0 g, 118 mmol) in tetrahydrofuran (150 mL) was stirred for 10 minutes at room temperature. At 0° C., a solution of 2,2-dimethylhexan-3-one (15.0 g, 117 mmol) in tetrahydrofuran (150 mL) was added dropwise with stirring within 30 minutes, and stirring was continued for 4 h at room temperature. In a second flask, but-3-yn-2-ol (9.00 g, 128 mmol) in tetrahydrofuran (200 mL) was added dropwise within 1 h to a stirred solution of ethyl magnesium chloride in tetrahydrofuran (2 M, 140 mL, 280 mmol). The resulting reaction mixture was refluxed for 3.5 h and allowed to cool to room temperature, prior to the dropwise addition to the above prepared cerium trichloride/2,2-dimethylhexan-3-one suspension within 45 minutes. After stirring at 45° C. for 2 h and at room temperature for 16 h, the reaction mixture was poured into ice/water (200 mL), acidified with 5 M aqueous hydrochloric acid (70 mL) to pH 1, and extracted with ether (2×600 mL). The combined organic extracts were washed with brine (2×400 mL), dried ($Na_2SO_4$), and concentrated under reduced pressure. Flash chromatography (400 g silica gel, pentane-ether, 2:1; $R_f$=0.17, 1:1) of the resulting residue furnished 5-tert-butyloct-3-yne-2,5-diol (19.5 g, 84%) as an odorless, slightly yellowish liquid, which crystallized rapidly after short immersion in a cooling bath at −78° C. (Mp: 56.3-57.2° C.).

A suspension of manganese dioxide (90%, 214 g, 2.22 mol) and 5-tert-butyloct-3-yne-2,5-diol (44.0 g, 222 mmol) in dichloromethane (400 mL) was stirred overnight at room temperature. The insoluble material was removed by filtration over a pad of Celite, and washed thoroughly with dichloromethane. The filtrate and the washings were combined and concentrated under reduced pressure. Flash chromatography (800 g silica gel, pentane-ether, 5:1; $R_f$=0.25) of the resulting residue furnished 5-tert-butyl-5-hydroxyoct-3-yn-2-one (33.8 g, 78%) as a slightly yellowish liquid.

During the course of 3 h, a solution of methanesulfonic anhydride (387 g, 2.22 mol) in dichloromethane (1.5 L) was added at 0° C. to a stirred solution of 5-tert-butyl-5-hydroxyoct-3-yn-2-one (55.1 g, 253 mmol) and triethylamine (616 mL, 450 g, 4.45 mol) in dichloromethane (1.5 L). The resulting reaction mixture was then allowed to warm to room temperature, and stirred for 30 min at that temperature, prior to being poured into ice-cold concentrated aqueous hydrochloric acid (500 mL). The product was extracted with dichloromethane (2×1000 mL), and the combined organic extracts were washed with water (2×1000 mL), dried over $Na_2SO_4$, and concentrated to afford the crude product as an orange-colored oil. Purification by gradient chromatography (1 kg silica gel, pentane-ether, 40:1/20:1; $R_f$=0.10, 40:1) provided (5Z)-5-tert-butyloct-5-en-3-yn-2-one (24.6 g, 55%) as a yellowish oil.

A solution of (5Z)-5-tert-butyloct-5-en-3-yn-2-one (21.5 g, 121 mmol) in tetrahydrofuran (100 mL) was added dropwise within 30 minutes to a stirred suspension of lithium aluminium hydride (9.64 g, 241 mmol) in tetrahydrofuran (100 mL), upon which the temp. rose to 50° C. The reaction mixture was allowed to cool to room temperature, and stirring was continued at this temperature overnight. At 0° C., the reaction was quenched by dropwise addition of water (100 mL), 2 M aqueous sodium hydroxide solution (50 mL) and water (100 mL), and then poured into water (100 mL). The product was extracted with ether (2×300 mL), and the combined organic extracts were washed with brine (2×200 mL), dried ($Na_2SO_4$), and concentrated under reduced pressure. Flash chromatography (400 g silica gel, pentane-ether, 5:1; $R_f$=0.27) of the resulting residue furnished (3E,5E)-5-tert-butylocta-3,5-dien-2-ol (14.9 g, 62%) as a slightly yellowish liquid.

Odor description: green-floral, rooty, slightly carrot, with orris facets.

IR (neat): 3322 (br m, OH), 1459 (m, $CH_2$, $CH_3$), 1390 (m), 1361 (m, $C(CH_3)_3$), 1140 (m), 1059 (s, C—O), 970 (s, $CH_3CO$), 942 (m, CC), 889 (m, C=CH) cm$^{-1}$. $^1$H NMR (CDCl$_3$): δ=0.94 (t, J=7.5 Hz, 3H, 8-$H_3$), 1.04 (s, 9H, $Me_3C$-1'), 1.32 (d, J=6.5 Hz, 3H, 1-$H_3$), 1.62 (s, 1H, 2-OH), 2.10 (ddq, J=1.0, 7.0, 7.5 Hz, 2H, 7-$H_2$), 4.38 (ddq, J=1.0, 6.5, 6.5 Hz, 1H, 2-H), 5.30 (t, J=7.0 Hz, 1H, 6-H), 5.54 (dd, J=6.5, 16.0 Hz, 1H, 3-H), 6.05 (dd, J=1.0, 16.0 Hz, 1H, 4-H). NOESY ($^1$H/$^1$H): 3-H/4-H, $Me_3C$-1'/6-H. $^{13}$C NMR (CDCl$_3$): δ=14.9 (q, C-8), 22.5 (t, C-7), 23.6 (q, C-1), 29.6 (3q, $Me_3C$-1'), 35.3 (s, C-1'), 69.3 (d, C-2), 125.4 (d, C-6), 126.4 (d, C-3), 137.6 (d, C-4), 145.2 (s, C-5). MS: m/z (%)=29 (12) [$C_2H_5^+$], 43 (66) [$C_3H_7^+$], 57 (74) [$C_4H_9^+$], 69 (52) [$C_5H_9^+$], 81 (35) [$M^+$-$C_4H_9$—$C_3H_9$], 95 (35) [$C_7H_{11}^+$], 109 (100) [$C_8H_{13}^+$], 124 (29) [$M^+$-$CH_3CO$—$CH_3$], 139 (5) [$M^+$-$CH_3CO$], 149 (10) [$M^+$-$H_2O$—$CH_3$], 164 (8) [$M^+$-$H_2O$], 182 (2) [$M^+$]. Anal. Calcd for $C_{12}H_{22}O$ (182.31): C, 79.06; H, 12.16. Found: C, 78.70; H, 12.22.

Manganese dioxide (66.3 g, 686 mmol) was added to a stirred solution of (3E,5E)-5-tert-butylocta-3,5-dien-2-ol (13.9 g, 68.6 mmol) in dichloromethane (200 mL). The reaction mixture was stirred overnight at room temperature, prior to removal of the insoluble material by filtration over a pad of Celite, and thorough washing with dichloromethane. The filtrate and the washings were combined and concentrated under reduced pressure. Flash chromatography (380 g silica gel, pentane-ether, 30:1; $R_f$=0.27) of the resulting residue afforded (3E,5E)-5-tert-butylocta-3,5-dien-2-one (10.0 g, 81%) as a slightly yellowish liquid.

Odor description: orris, irone, sweet-violet, with carrot-like and woody-leathery undertones.

IR (neat): 1695 (m, C=C, asym.), 1672 (s, C=O), 1611 (m, C=C), 1478 (w), 1462 (m), 1394 (w, $CH_2$, $CH_3$), 1360 (s, $C(CH_3)_3$), 1248 (s), 1172 (s, $CH_2$, $CH_3$), 980 (s, C=C, 1,2-trans), 867 (m, C=CH) cm$^{-1}$. $^1$H NMR (CDCl$_3$): δ=0.98 (t, J=7.5 Hz, 3H, 8-$H_3$), 1.09 (s, 9H, $Me_3C$-1'), 2.14 (ddq, J=1.0, 7.5, 7.5 Hz, 2H, 7-$H_2$), 2.31 (s, 3H, 1-$H_3$), 5.56 (t, J=7.5 Hz, 1H, 6-H), 6.11 (d, J=16.5 Hz, 1H, 3-H), 7.21 (td, J=1.0, 16.5 Hz, 1H, 4-H). NOESY ($^1$H/$^1$H): 3-H/4-H, $Me_3C$-1'/6-H. $^{13}$C NMR (CDCl$_3$): δ=14.6 (q, C-8), 22.7 (t, C-7), 27.2 (q, C-1), 29.7 (3q, $Me_3C$-1'), 35.5 (s, C-1'), 130.2 (d, C-6), 132.2 (d, C-3), 142.2 (d, C-4), 143.9 (s, C-5), 198.4 (s, C-2). MS: m/z (%)=43 (32) [$CH_3CO^+$], 57 (15) [$C_4H_9^+$], 81 (13) [$M^+$-$C_4H_9$—$C_2H_2O$], 91 (9) [$C_7H_7^+$], 95 (31) [$M^+$-$CH_3CO$—$C_3H_6$], 109 (9) [$M^+$-$C_2H_5$—$C_2H_2O$], 123 (28) [$M^+$-$C_4H_9$], 137 (12) [$M^+$-$CH_3CO$], 151 (100) [$M^+$-$C_2H_5$], 165 (2) [$M^+$-$CH_3$], 180 (8) [$M^+$]. Anal. Calcd for $C_{12}H_{20}O$ (180.29): C, 79.94; H, 11.18. Found: C, 79.86; H, 11.35.

EXAMPLE 2

(3E,5E)-5-(tert-Pentyl)octa-3,5-dien-2-one (R=H, $R^1$=Me, $\Delta^{2,5}$)

A solution of tert-pentylmagnesium chloride in tetrahydrofuran (0.6 M, 1000 mL, 600 mmol) [prepared from magnesium (25.5 g, 1.05 mol) and a solution of 2-chloro-2-methylbutane (98 g, 919 mmol) in tetrahydrofuran (1000 mL); titrated with a solution of rac-menthol in THF, using 1,10-phenanthrolin as indicator] was added at room temperature within 5 h to a stirred solution of butyryl chloride (63.9 g, 600 mmol) and copper(I) chloride (2.97 g, 30.0 mmol, 5.0 mol %) in tetrahydrofuran (450 mL). The resulting reaction mixture was then stirred for 17 h, prior to being poured into ice-cold 2 M aqueous hydrochloric acid (500 mL). The product was extracted with ether (2×600 mL), and the combined organic extracts were washed with brine (2×400 mL), dried ($Na_2SO_4$), and concentrated under reduced pressure. Distillation (93° C./102 mbar) of the crude product afforded the title compound 3,3-dimethylheptan-4-one (65.8 g, 69%; GC-purity: 89%) as a colorless liquid, which was used without further purification.

As described in Example 1 for the synthesis of 5-tert-butyloct-3-yne-2,5-diol, from a solution of cerium trichloride (95.0 g, 386 mmol) in tetrahydrofuran (550 mL), a solution of the previously prepared 3,3-dimethylheptan-4-one (89%, 58.7 g, 367 mmol) in tetrahydrofuran (550 mL), a solution of but-3-yn-2-ol (28.3 g, 404 mmol) in tetrahydrofuran (600 mL), and an ethyl magnesium chloride solution in tetrahydrofuran (2 M, 440 mL, 881 mmol). Standard workup, purification by gradient chromatography (1.8 kg silica gel, pentane-ether, 3:1/1:1/1:3; $R_f$=0.36, 2:1) and drying in vacuo (45° C., 0.20 mbar) afforded the diastereomeric 6,6-dimethyl-5-propyloct-3-yne-2,5-diol (54.4 g, 70%) as an odorless, slightly orange-colored, viscous oil.

As described in Example 1 for the synthesis of 5-tert-butyl-5-hydroxyoct-3-yn-2-one, from 6,6-dimethyl-5-propyloct-3-yne-2,5-diol (54.1 g, 255 mmol) with a suspension of manganese dioxide (90%, 365 g, 3.78 mol) in dichloromethane (1 L). Filtration over a short pad of Celite, and thorough washing of the filter cake with dichloromethane, followed by gradient chromatography (1.8 kg silica gel, pentane-ether, 9:1/4:1/1:1; $R_f$=0.40, 10:1) furnished 5-hydroxy-6,6-dimethyl-5-propyloct-3-yn-2-one (47.0 g, 88%) as a yellowish liquid.

As described in Example 1 for the synthesis of (5Z)-5-tert-butyloct-5-en-3-yn-2-one, from a solution of methanesulfonic anhydride (2.50 g, 14.4 mmol) in dichloromethane (12 mL), a stirred solution of 5-hydroxy-6,6-dimethyl-5-propyloct-3-yn-2-one (300 mg, 1.43 mmol) and triethylamine (4.0 mL, 2.92 g, 28.9 mmol) in dichloromethane (10 mL), and quenching with 2 M aqueous hydrochloric acid (20 mL). Standard workup and purification by flash chromatography (38 g silica gel, pentane-ether, 50:1; $R_f$=0.33, 50:1) provided the (Z)-5-(tert-pentyl)oct-5-en-3-yn-2-one (190 mg, 69%) as a yellowish oil.

As described in Example 1 for the synthesis of (3E,5E)-5-tert-butylocta-3,5-dien-2-ol, from a solution of (Z)-5-(tert-pentyl)oct-5-en-3-yn-2-one (3.83 g, 19.9 mmol) in tetrahydrofuran (40 mL) with a stirred suspension of $LiAlH_4$ (1.80 g, 47.4 mmol) in tetrahydrofuran (30 mL). At 0° C., the reaction was quenched by dropwise addition of water (5 mL) and 2 M aqueous hydrochloric acid solution (10 mL). Standard workup and purification by flash chromatography (400 g silica gel, pentane-ether, 5:1; $R_f$=0.27, 5:1) furnished (3E,5E)-5-(tert-pentyl)octa-3,5-dien-2-ol (3.62 g, 93%) as a slightly yellowish liquid.

Odor description: fruity, pear, grapefruit, slightly leathery.

IR (neat): 3322 (br m, OH), 1458 (m, $CH_2$, $CH_3$), 1375 (m, $C(CH_3)_2$), 1139 (m), 1059 (s, C—O), 970 (s, $CH_3$—CO), 942 (m, C—C), 858 (m, C=C—H) $cm^{-1}$. $^1H$ NMR ($CDCl_3$): δ=0.70 (t, J=7.5 Hz, 3H, 3'-$H_3$), 0.94 (t, J=7.5 Hz, 3H, 8-$H_3$), 0.99 (s, 6H, 1'-$Me_2$), 1.31 (d, J=6.5 Hz, 3H, 1-$H_3$), 1.33 (q, J=7.5 Hz, 2H, 2'-$H_2$), 1.76 (s, 1H, 2-OH), 2.11 (ddq, J=1.0, 7.0, 7.5 Hz, 2H, 7-$H_2$), 4.37 (ddq, J=1.0, 6.5, 6.5 Hz, 1H, 2-H), 5.25 (t, J=7.0 Hz, 1H, 6-H), 5.53 (dd, J=6.5, 16.0 Hz, 1H, 3-H), 6.05 (dd, J=1.0, 16.0 Hz, 1H, 4-H). $^{13}C$ NMR ($CDCl_3$): δ=8.7 (q, C-3'), 15.0 (q, C-8), 22.5 (t, C-7), 23.6 (q, C-1), 27.1 (2q, $Me_2$C-1'), 33.6 (t, C-2'), 38.5 (s, C-1'), 69.2 (d, C-2), 126.4 (d, C-6), 127.3 (d, C-3), 137.5 (d, C-4), 143.1 (s, C-5). MS: m/z (%)=43 (100) [$CH_3CO^+$], 45 (14) [$C_2H_5O+$], 55 (33) [$C_4H_7^+$], 57 (17) [$C_4H_9^+$], 67 (21) [$M^+$-$C_5H_{11}$—$CH_3$—$C_3H_7$], 69 (22) [$C_5H_9^+$], 71 (41) [$C_5H_{11}^+$], 77 (17) [$M^+$-$C_2H_5$—$C_3H_8$—$H_2O$—$C_2H_4$], 79 (23) [$M^+$-$C_2H_5$—$H_2O$—$C_2H_4$—$C_3H_6$], 81 (32) [$M^+$-$C_2H_5$—$C_3H_6O$—$C_2H_4$], 83 (14) [$C_6H_{11}^+$], 91 (23) [$C_7H_7^+$], 93 (26) [$M^+$-$C_2H_5$—$H_2O$—$C_4H_8$], 95 (22) [$M^+$-$C_2H_5$—$C_3H_8$—$C_2H_4$], 97 (13) [$M^+$-$C_5H_{10}$—$C_2H_5$], 105 (11) [$M^+$-$C_2H_5$—$C_3H_8$—$H_2O$], 107 (35) [$M^+$-$C_5H_{11}$—$H_2O$], 108 (11) [$M^+$-$C_5H_{10}$—$H_2O$], 109 (45) [$M^+$-$C_2H_5$—$C_3H_6O$], 110 (28) [$M^+$-$C_5H_{11}$—$CH_3$], 121 (17) [$M^+$-$C_2H_5$—$H_2O$—$C_2H_4$], 123 (26) [$M^+$-$C_2H_5$—$C_3H_8$], 125 (12) [$M^+$-$C_5H_{11}$], 126 (16) [$M^+$-$C_5H_{10}$], 149 (29) [$M^+$-$C_2H_5$—$H_2O$], 167 (9) [$M^+$-$C_2H_5$], 178 (7) [$M^+$-$H_2O$], 196 (2) [$M^+$]. Anal. Calcd for $C_{13}H_{24}O$ (196.33): C, 79.53; H, 12.32. Found: C, 79.32; H, 12.37.

As described in Example 1 for the synthesis of the title compound (3E,5E)-5-tert-butylocta-3,5-dien-2-one, from (3E,5E)-5-(tert-pentyl)octa-3,5-dien-2-ol (3.41 g, 17.3 mmol) and a suspension of manganese dioxide (90%, 24.1 g, 249 mmol) in dichloromethane (100 mL). Filtration over a short pad of Celite, and thorough washing of the filter cake with dichloromethane, followed by purification by flash chromatography (350 g silica gel, pentane-ether, 30:1; $R_f$=0.24, 30:1) afforded (3E,5E)-5-(tert-pentyl)octa-3,5-dien-2-one (3.02 g, 90%) as a yellowish liquid.

Odor description: orris, honey, tobacco, hay, floral-green.

IR (neat): 1695 (m, C=C, asym.), 1672 (s, C=O), 1610 (m, C=C), 1459 (m, $CH_2$, $CH_3$), 1359 (s, $C(CH_3)_2$), 1250 (s), 1172 (s, $CH_2$, $CH_3$), 980 (s, C=C, 1,2-trans), 866 (m, C=C—H) $cm^{-1}$. $^1H$ NMR ($CDCl_3$): δ=0.72 (t, J=7.5 Hz, 3H, 3'-$H_3$), 0.98 (t, J=7.5 Hz, 3H, 8-$H_3$), 1.05 (s, 6H, 1'-$Me_2$), 1.39 (q, J=7.5 Hz, 2H, 2$H_2$), 2.15 (ddq, J=1.0, 7.0, 7.5 Hz, 2H, 7-$H_2$), 2.30 (s, 3H, 1-$H_3$), 5.49 (t, J=7.0 Hz, 1H, 6-H), 6.10 (d, J=16.5 Hz, 1H, 3-H), 7.13 (td, J=1.0, 16.5 Hz, 1H, 4-H). $^{13}C$ NMR ($CDCl_3$): δ=8.7 (q, C-3'), 14.8 (q, C-8), 22.8 (t, C-7), 27.3 (2q, $Me_2$C-1'), 33.9 (t, C-2'), 38.8 (s, C-1'), 131.7 (d, C-6), 132.2 (d, C-3), 141.9 (s, C-5), 142.3 (d, C-4), 198.4 (s, C-2). MS: m/z (%)=43 (100) [$CH_3CO^+$], 55 (12) [$C_4H_7^+$], 67 (6) [$C_5H_7^+$], 71 (9) [$C_5H_{11}^+$], 77 (10) [$C_6H_5^+$], 79 (11) [$M^+$-$C_2H_5$—$C_3H_6$—$C_2H_4O$], 81 (12) [$M^+$-$C_2H_5$—$C_2H_2O$—$C_2H_6$], 91 (11) [$C_7H_7^+$], 93 (8) [$M^+$-$C_2H_5$—$C_2H_4O$—$C_2H_4$], 95 (24) [$M^+$-$C_2H_5$—$C_2H_2O$—$C_2H_4$], 107 (13) [$M^+$-$C_2H_5$—$C_2H_4$—$CH_2O$], 109 (11) [$M^+$-$CH_3CO$—$C_3H_6$], 121 (16) [$M^+$-$C_2H_5$—$C_2H_4O$], 123 (40) [$M^+$-$C_2H_5$—$C_2H_2O$], 137 (7) [$M^+$-$C_2H_5$—$C_2H_4$], 151 (8) [$M^+$-$CH_3CO$], 165 (66) [$M^+$-$C_2H_5$], 179 (2) [$M^+$-$CH_3$], 194 (7) [$M^+$]. Anal. Calcd for $C_{13}H_{22}O$ (194.32): C, 80.35; H, 11.41. Found: C, 80.63; H, 11.56.

EXAMPLE 3

(3E,5E)-5-(tert-Butyl)-7-methylnona-3,5-dien-2-one ($R=Me$, $R^1=H$, $\Delta^{2,5}$)

At room temperature under $N_2$ atmosphere, DMF (7 drops, 0.110 g, 1.50 mmol) was added to 3-methylpentanoic acid (50.0 g, 0.430 mol). Over a period of 2 h, thionyl chloride (77.0 g, 0.647 mol) was added slowly with stirring, upon which the temp. dropped to 12° C. with vigorous gas evolution. After 30 minutes of further stirring at room temperature, the temperature was slowly increased to 80° C., and the reaction mixture then refluxed for 2 h. Distillation of the crude material afforded at 73° C./200 mbar 3-methylpentanoyl chloride (47.8 g, 83%) as a colorless liquid.

As described in Example 2 for 3,3-dimethylheptan-4-one, from a 2.0 M solution of tert-butyl magnesium chloride in ether (178 mL, 355 mmol), a stirred solution of 3-methylpentanoyl chloride (47.8 g, 355 mmol) and copper(I) chloride (1.76 g, 17.8 mmol, 5.0 mol %) in ether (270 mL). Standard workup and distillation (120-122° C./180 mbar) of the resulting residue afforded 2,2,5-trimethylheptan-3-one (34.9 g, 63%) as a colorless liquid.

At room temperature, a solution of 2,2,5-trimethylheptan-3-one (4.69 g, 30.0 mmol) in tetrahydrofuran (15 mL), was added dropwise within 50 minutes to a stirred 0.6 M solution of $LaCl_3 \cdot 2LiCl$ in tetrahydrofuran (50 mL, 30 mmol). Stirring was continued at that temp. for 1 h. In a second flask, but-3-yn-2-ol (2.31 g, 33 mmol) in tetrahydrofuran (50 mL) was added dropwise within 2 h to a stirred solution of EtMgCl in THF (2 M, 36 mL, 72 mmol). The resulting reaction mixture was refluxed for 3.5 h and allowed to cool to room temperature, prior to the dropwise addition to the above prepared $LaCl_3 \cdot 2LiCl/2,2,5$-trimethylheptan-3-one solution within 2.5 h. After stirring at reflux overnight, the reaction mixture was allowed to cool to room temperature, and worked up as described in Example 1 for the synthesis of 5-tert-butyloct-3-yne-2,5-diol. Flash chromatography (180 g silica gel, pentane-ether, 2:1; $R_f$=0.19, 2:1) provided 5-tert-butyl-7-methylnon-3-yn-2,5-diol (1.60 g, 24%) as an odorless, colorless solid (Mp: 41.0-43.3° C.).

As described for the synthesis of 5-tert-butyl-5-hydroxyoct-3-yn-2-one in Example 1, from tert-butyl-7-methylnon-3-yn-2,5-diol (33.0 g, 146 mmol) and a suspension of manganese dioxide (90%, 190 g, 1.97 mol) in dichloromethane (580 mL). Filtration over a short pad of Celite, and thorough washing of the filter cake with dichloromethane, followed by gradient chromatography (1 kg silica gel, pentane-ether, 9:1; $R_f$=0.12, 9:1) furnished 5-tert-butyl-5-hydroxy-7-methylnon-3-yn-2-one (27.5 g, 84%) as a colorless liquid.

As described in Example 1 for the synthesis of 5-tert-butyl-5-hydroxyoct-3-yn-2-one, from a solution of methanesulfonic anhydride (100 g, 574 mmol) in dichloromethane (395 mL), a stirred solution of 5-tert-butyl-5-hydroxy-7-methylnon-3-yn-2-one (14.6 g, 65.2 mmol) and triethylamine (182 mL, 132 g, 1.31 mmol) in dichloromethane (415 mL), and quenching with 2 M aqueous hydrochloric acid (400 mL). Standard workup and purification by gradient chromatography (600 g silica gel, pentane-ether, 98:2; $R_f$=0.15, 98:2) provided (Z)-5-tert-butyl-7-methylnon-5-en-3-yn-2-one (10.4 g, 75%) as a yellowish oil.

As described in Example 1 for the synthesis of (3E,5E)-5-tert-butylocta-3,5-dien-2-ol, from a solution of (Z)-5-tert-butyl-7-methylnon-5-en-3-yn-2-one (9.90 g, 48.0 mmol) in tetrahydrofuran (95 mL) and a stirred suspension of lithium aluminium hydride (4.37 g, 115 mmol) in tetrahydrofuran (75 mL). At 0° C., the reaction was quenched by dropwise addition of water (30 mL) and 5 M aqueous hydrochloric acid solution (50 mL). Standard workup and purification by flash chromatography (600 g silica gel, pentane-ether, 9:1; $R_f$=0.2, 9:1) furnished (3E,5E)-5-(tert-butyl)-7-methylnona-3,5-dien-2-ol (7.80 g, 77%) as a colorless liquid.

Odor description: very weak, fatty-oily, slightly fruity-musky.

IR (neat): 3326 (br m, O—H), 1478 (m, $CH_2$, $CH_3$), 1361 (m, $C(CH_3)_2$), 1141 (m), 1062 (s, C—O), 969 (s, $CH_3$—CO), 942 (m, C—C), 872, 853 (m, C═C—H) $cm^{-1}$. $^1H$ NMR ($CDCl_3$): δ=0.79/0.80 (2 t, J=7.5 Hz, 3H, 9-$H_3$), 0.90/0.91 (2 d, J=6.5 Hz, 3H, 1"-$H_3$), 1.02/1.03 (s, 9H, 1'-$Me_3$), 1.14-1.30 (m, 2H, 8-$H_2$), 1.32 (d, J=6.5 Hz, 3H, 1-$H_3$), 1.55 (br s, 1H, 2-OH), 2.35 ($m_c$, 1H, 7-H), 4.37 (quint, J=6.5 Hz, 1H, 2-H), 5.03 (d, J=10.0 Hz, 1H, 6-H), 5.51 (dd, J=6.5 Hz, 16.0 Hz, 1H, 3-H), 6.05 (d, J=16.0 Hz, 1H, 4-H). $^{13}C$ NMR ($CDCl_3$): δ=11.9 (q, C-9), 21.3 (q, C-1"), 23.6 (q, C-1), 29.6 (3q, $Me_3C$-1'), 30.7 (t, C-8), 34.4 (s, C-1'), 35.3 (d, C-7), 69.3 (d, C-2), 127.0 (d, C-6), 130.0 (d, C-3), 137.0 (d, C-4), 144.8 (s, C-5). MS: m/z (%)=29 (14) [$CHO^+$], 43 (75) [$CH_3CO^+$], 57 (100) [$C_4H_9^+$], 69 (23) [$C_5H_9^+$], 81 (30) [$C_6H_9^+$], 95 (56) [$C_7H_{11}^+$], 109 (72) [$M^+$-$C_2H_5O$—$C_4H_8$], 137 (49) [$M^+$-$C_2H_5O$—$C_2H_4$], 153 (22) [$M^+$-$C_4H_9$], 165 (28) [$M^+$-$C_2H_5O$], 177 (2) [$M^+$-$CH_3$-water], 195 (1) [$M^+$-$CH_3$], 210 (4) [$M^+$]. HRMS-EI: m/z [$M^+$] calcd for $C_{14}H_{26}O$: 210.19837. found: 210.19733.

As described in Example 1 for the synthesis of the title compound (3E,5E)-5-tert-butylocta-3,5-dien-2-one, from (3E,5E)-5-(tert-butyl)-7-methylnona-3,5-dien-2-ol (7.80 g, 37.1 mmol) and a suspension of manganese dioxide (90%, 48.4 g, 501 mmol) in dichloromethane (140 mL). Filtration over a short pad of Celite, and thorough washing of the filter cake with dichloromethane, followed by purification by flash chromatography (600 g silica gel, pentane-ether, 19:1; $R_f$=0.17, 19:1) afforded (3E,5E)-5-(tert-butyl)-7-methylnona-3,5-dien-2-one (4.90 g, 64%) as a colorless liquid.

Odor description: orris, woody-ambery, ionone, slightly fruity and peppery.

IR (neat): 1697 (m, C═C, asym.), 1676 (s, C═O), 1614 (m, C═C), 1461 (m, $CH_2$, $CH_3$), 1359 (s, $C(CH_3)_2$), 1250 (s), 1169 (m, $CH_2$, $CH_3$), 981 (m, C═C, 1,2-trans), 877 (w, C═C—H) $cm^{-1}$. $^1H$ NMR ($CDCl_3$): δ=0.81 (t, J=7.5 Hz, 3H, 9-$H_3$), 0.94 (d, J=7.0 Hz, 3H, 1"-$H_3$), 1.10 (s, 9H, 1'-$Me_3$), 1.23 (dqd, J=7.0 Hz, 7.5 Hz, 13.5 Hz, 1H, 8-$H_b$), 1.38 (dqd, J=6.0 Hz, 7.5 Hz, 13.5 Hz, 1H, 8-$H_a$), 2.31 (s, 3H, 1-$H_3$), 2.35 ($m_c$, 1H, 7-H), 5.29 (d, J=10.0 Hz, 1H, 6-H), 6.11 (d, J=16.5 Hz, 1H, 3-H), 7.22 (d, J=16.5 Hz, 1H, 4-H). $^{13}C$ NMR ($CDCl_3$): δ=11.8 (q, C-9), 21.1 (q, C-1"), 27.2 (q, C-1), 29.8 (3q, $Me_3C$-1'), 30.5 (t, C-8), 34.7 (d, C-7), 35.5 (s, C-1'), 131.8 (d, C-6), 134.5 (d, C-3), 142.8 (d, C-4), 143.5 (s, C-5), 198.4 (s, C-2). MS: m/z (%)=43 (100) [$CH_3CO^+$], 57 (56) [$C_4H_9^+$], 67 (10) [$C_5H_7^+$], 77 (14) [$C_6H_5^+$], 91 (16) [$C_7H_7^+$], 95 (35) [$C_7H_{11}^+$], 109 (68) [$M^+$-$CH_3CO$—$C_4H_8$], 123 (47) [$M^+$-$C_2H_5$—$C_3H_4O$], 137 (14) [$M^+$-$C_2H_5$—$C_2H_2O$], 151 (48) [$M^+$-$C_4H_9$], 165 (60) [$M^+$-$CH_3CO$], 179 (2) [$M^+$-$C_2H_5$], 193 (1) [$M^+$-$CH_3$], 208 (1) [$M^+$]. HRMS-EI: m/z [$M^+$] calcd for $C_{14}H_{24}O$: 208.18272. found: 208.18195.

EXAMPLE 4

5-tert-Butyloctan-2-one ($R=R^1=H$)

A solution of (3E,5E)-5-tert-butylocta-3,5-dien-2-one from Example 1 (1.50 g, 8.32 mmol) and Pd/C (10%, 50.0 mg) in ethanol (30 mL) was stirred under hydrogen atmosphere overnight. The insoluble materials were removed by filtration through a pad of Celite, and thoroughly washed with ethanol. Removal of the solvent under reduced pressure and flash chromatography (70 g silica gel, pentane-ether, 50:1; $R_f$=0.15) afforded 5-tert-butyloctan-2-one (1.26 g, 82%) as a yellowish liquid.

Odor description: orris roots, natural, green-fatty, with carrot-like and slightly fruity facets.

IR (neat): 1716 (s, C═O), 1474 (m, $CH_2$, $CH_3$), 1364 (s $C(CH_3)_3$), 1229 (s), 1159 (s, C—CO, asym.) $cm^{-1}$.

¹H NMR (CDCl₃): δ=0.83-0.92 (m, 1H, 6-H$_b$), 0.87 (s, 9H, Me₃C-1'), 0.89 (t, J=7.0 Hz, 3H, 8-H₃), 0.94-1.05 (dddd, J=5.0, 7.0, 13.0, 15.0 Hz, 1H, 6-H$_a$), 1.19-1.43 (m, 3H, 5-H, 7-H₂), 1.43 (dddd, J=3.5, 5.5, 10.5, 14.0 Hz, 1H, 4-H$_b$) 1.76 (dddd, J=3.5, 6.0, 11.0, 14.0 Hz, 1H, 4-H$_a$), 2.14 (s, 3H, 1-H₃), 2.40 (ddd, J=6.0, 10.5, 16.5 Hz, 1H, 3-H$_b$), 2.49 (ddd, J=5.5, 11.0, 16.5 Hz, 1H, 3-H$_a$). ¹³C NMR (CDCl₃): δ=14.6 (q, C-8), 23.2 (t, C-7), 25.3 (t, C-4), 27.7 (3q, Me₃C-1'), 29.8 (q, C-1), 33.5 (t, C-6), 33.9 (s, C-1'), 44.1 (t, C-3), 48.0 (d, C-5), 209.3 (s, C-2). MS: m/z (%)=43 (87) [CH₃CO⁺], 57 (84) [C₄H₉⁺], 58 (100) [C₃H₆O⁺], 69 (41) [M⁺-C₄H₉—C₃H₆O], 83 (27) [M⁺-C₄H₉—C₃H₈], 109 (54) [M⁺-CH₃—H₂O—C₃H₆], 127 (62) [M⁺-C₄H₉], 151 (11) [M⁺-CH₃—H₂O], 169 (1) [M⁺-CH₃], 184 (1) [M⁺]. Anal. Calcd for C₁₂H₂₄O (184.32): C, 78.20; H, 13.12. Found: C, 78.24; H, 13.11.

EXAMPLE 5

6,6-Dimethyl-5-propyloctan-2-one (R=H, R¹=Me)

As described for the synthesis of 5-tert-butyloctan-2-one in Example 4, from a solution of (3E,5E)-5-(tert-pentyl) octa-3,5-dien-2-one (1.26 g, 6.49 mmol) from Example 2, and Pd/C (10%, 50.0 mg) in ethanol (30 mL). Filtration over a short pad of Celite, and thorough washing of the filter cake with ethanol, followed by flash chromatography (65 g silica gel, pentane-ether, 50:1; R$_f$=0.26, 50:1) afforded 6,6-dimethyl-5-propyloctan-2-one (1.15 g, 89%) as a pale yellow liquid.

Odor description: peppery, woody-orris.

IR (neat): 1716 (s, C=O), 1462 (m, CH₂, CH₃), 1356 (m, C(CH₃)₂), 1157 (m, C—CO, asym.) cm⁻¹. ¹H NMR (CDCl₃): δ=0.79 (t, J=7.5 Hz, 3H, 8-H₃), 0.80 (s, 6H, 6-Me₂), 0.89 (t, J=7.0 Hz, 3H, 3'-H₃), 0.94-1.03 (m, 2H, 1'-H₂), 1.17-1.46 (m, 4H, 4-H$_b$, 5-H, 2'-H₂), 1.28 (q, J=7.5 Hz, 2H, 7-H₂), 1.75 (dddd, J=3.0, 6.0, 11.0, 14.0 Hz, 1H, 4-H$_a$), 2.14 (s, 3H, 1-H₃), 2.39 (ddd, J=6.0, 10.5, 16.5 Hz, 1H, 3-H$_b$), 2.49 (ddd, J=5.5, 11.0, 16.5 Hz, 1H, 3-H$_a$). ¹³C NMR (CDCl₃): δ=8.2 (q, C-8), 14.7 (q, C-3'), 23.3 (t, C-2'), 24.2 (3q, 6-Me₂), 25.0 (t, C-4), 29.8 (q, C-1), 32.5 (t, C-7), 33.2 (t, C-1'), 36.3 (s, C-6), 44.2 (t, C-3), 45.6 (d, C-5), 209.3 (s, C-2). MS: m/z (%)=43 (100) [CH₃CO⁺], 55 (29) [C₄H₇⁺], 58 (64) [C₃H₆O⁺], 59 (23) [M⁺-C₄H₅O—C₅H₁₀], 69 (27) [M⁺-C₅H₁₁—C₃H₆O], 70 (44) [C₅H₁₀⁺], 71 (59) [C₅H₁₁⁺], 81 (3) [M⁺-C₂H₅—H₂O—C₃H₆—C₂H₄], 83 (8) [M⁺-C₅H₁₁—C₃H₈], 85 (9) [M⁺-C₅H₁₀—CH₃CO], 95 (6) [M⁺-C₂H₅—H₂O—C₅H₁₀], 109 (14) [M⁺-C₂H₅—H₂O—C₃H₆], 113 (4) [M⁺-C₅H₁₀—CH₃], 127 (21) [M⁺-C₅H₁₁], 128 (14) [M⁺-C₅H₁₀], 129 (11) [M⁺-C₄H₅O], 151 (8) [M⁺-C₂H₅—H₂O], 165 (2) [M⁺-CH₃—H₂O], 169 (1) [M⁺-C₂H₅], 183 (1) [M⁺-CH₃], 198 (1) [M⁺]. Anal. Calcd for C₁₃H₂₆O (198.35): C, 78.72; H, 13.21. Found: C, 78.64; H, 13.18.

EXAMPLE 6

5-tert-Butyl-7-methylnonan-2-one (R=Me, R¹=H)

As described for the synthesis of 5-tert-butyloctan-2-one in Example 4, from a solution of (3E,5E)-5-(tert-butyl)-7-methylnona-3,5-dien-2-one (1.00 g, 4.80 mmol) and Pd/C (10%, 50.0 mg) in ethanol (27 mL). Filtration over a short pad of Celite, and thorough washing of the filter cake with ethanol, followed by flash chromatography (40 g silica gel, pentane-ether, 19:1; R$_f$=0.19, 19:1) afforded 5-tert-butyl-7-methylnonan-2-one (1.00 g, 98%) as a colorless liquid.

Odor description: fresh peppery, fruity-woody-citrusy, linalyl acetate, orris-like.

IR (neat): 1717 (s, C=O), 1463 (m, CH₂, CH₃), 1364 (m, C(CH₃)₂), 1159 (m, C—CO, asym.) cm⁻¹. ¹H NMR (CDCl₃): δ=0.77/0.79 (2t, J=6.5 Hz, 3H, 9-H₃), 0.84/0.86 (2d, J=6.5 Hz, 3H, 1''-H₃), 0.86 (br s, 9H, 1'-Me₃), 0.89-1.33 (m, 6H, 5-H, 6-H₂, 7-H, 8-H₂), 1.40 (m$_c$, 1H, 4-H$_b$), 1.76 (m$_c$, 1H, 4-H$_a$), 2.13/2.14 (2s, 3H, 1-H₃), 2.42 (br ddd, J=6.0, 6.0, 16.5 Hz, 1H, 3-H$_b$), 2.48 (br ddd, J=6.0, 6.0, 16.5 Hz, 1H, 3-H$_a$). ¹³C NMR (CDCl₃): δ=11.2/11.6 (2q, C-9), 19.0/20.1 (2q, C-1''), 25.7/25.9 (2t, C-4), 27.7 (6q, 1'-Me₃), 29.0/30.8 (2t, C-8), 29.8/29.9 (2q, C-1), 33.6/33.9 (2d, C-7), 33.9/34.0 (2s, C-1'), 38.6/38.7 (2t, C-6), 43.9/44.3 (2t, C-3), 45.0/45.1 (2d, C-5), 209.2/209.3 (2s, C-2). MS: m/z (%)=43 (92) [CH₃CO⁺], 57 (100) [C₄H₉⁺], 58 (97) [C₃H₆O⁺], 71 (24) [C₆H₁₁⁺], 83 (32) [M⁺-C₄H₈—H₂O—C₃H₆], 96 (26) [M⁺-C₄H₈—H₂O—C₂H₄], 109 (12) [M⁺-C₅H₁₁—H₂O], 123 (7) [M⁺-C₄H₉—H₂O], 137 (24) [M⁺-C₄H₉—H₂O], 155 (26) [M⁺-C₄H₉], 179 (1) [M⁺-CH₃—H₂O], 197 (1) [M⁺-CH₃], 212 (1) [M⁺].

HRMS-EI: m/z [M⁺] calcd for C₁₄H₂₈O: 212.21402. found: 212.21226.

EXAMPLE 7

Feminine Floral Fine Fragrance

| COMPOUND/INGREDIENT | PARTS PER WEIGHT 1/800 |
|---|---|
| 1. AMBERMAX 10%/TRIETHYLCITRATE (1,1,5,5-TETRAMETHYL-1,3,4,5,6,7-HEXAHYDRO- AND 1,1,5,5-TETRAMETHYL-1,3,4,5,6,8A-HEXAHYDRO-2H-2,4A-METHANONAPHTHALEN-8-YL)PROPAN-1-OL) | 3.00 |
| 2. AMBRETTOLIDE ((10E)-OXACYCLOHEPTADEC-10-EN-2-ONE) | 40.00 |
| 3. AMBROFIX (DODECAHYDRO-3A,6,6,9A-TETRAMETHYL-NAPHTHOL[2,1-B]FURAN) | 2.00 |
| 4. *ANGELICA* ROOT OIL | 2.50 |
| 5. BENZYL SALICYLATE | 55.00 |
| 6. CASHMERAN (1,2,3,5,6-HEXAHYDRO-1,1,2,3,3-PENTAMETHYL-4H-INDEN-4-ONE) | 25.00 |
| 7. CASSIONE (4-(1,3-BENZODIOXOL-5-YL)BUTAN-2-ONE) | 2.50 |
| 8. CUMARINE PURE CRYSTALLINE | 10.00 |
| 9. CYCLOMETHYLENE CITRONELLOL (3-(4-METHYLCYCLOHEX-3-EN-1-YL)BUTAN-1-OL) | 25.00 |
| 10. DIPROPYLENE GLYCOL (DPG) | 192.43 |
| 10. EBANOL (3-METHYL-5-(2,2,3-TRIMETHYL-3-CYCLOPENTEN-1-YL)-4-PENTEN-2-OL) | 10.00 |
| 11. EVERNYL (METHYL 3,6-DIMETHYLRESORCYLATE) | 1.00 |
| 12. GALBANUM OIL | 0.80 |
| 13. GEORGYWOOD (2-ACETYL-1,2,3,4,5,6,7,8-OCTAHYDRO-1,2,8,8-TETRAMETHYLNAPHTHALENE) | 120.00 |

| COMPOUND/INGREDIENT | PARTS PER WEIGHT 1/800 |
|---|---|
| 14. HELIOTROPINE CRYSTALLINE | 4.00 |
| 15. (3Z)-HEX-3-ENOL | 1.00 |
| 16. INDOL PURE | 0.35 |
| 17. ORRIS BUTTER | 0.80 |
| 18. ISORALDEINE KETONE ALPHA (3-METHYL-4-(2,6,6-TRIMETHYLCYCLOHEX-2-EN-1-YL)BUT-3-EN-2-ONE) | 45.00 |
| 19. JASMIN ABSOLUTE | 1.00 |
| 20. LINALOL, SYNTHETIC | 25.00 |
| 21. MANDARINE OIL | 25.00 |
| 22. MYSTIKAL (2-METHYLUNDECANOIC ACID) | 0.12 |
| 24. SERENOLIDE (2-(1'-(3'',3''-DIMETHYLCYCLOHEXYL)ETHOXY)-2-METHYLPROPYL CYCLOPROPANECARBOXYLATE) | 80.00 |
| 25. VANILLIN | 1.500 |
| 26. VELVIONE (CYCLOHEXADEC-5-ENE-1-ONE) | 55.00 |
| 27. VERTOFIX COEUR (COMMERCIAL ACETYL CEDRENE FRACTION) | 55.00 |
| 28. VETIVER OIL, MOLECULAR DESTILLATION QUALITY | 9.00 |
| 29. (3E,5E)-5-TERT-BUTYLOCTA-3,5-DIEN-2-ONE | 8.00 |
| | TOTAL: 800.00 |

At only 1%, (3E,5E)-5-tert-butylocta-3,5-dien-2-one (Example 1) provides a very natural and rich powdery-warm orris effect that extends the soft orris butter fond throughout the whole composition to the top note, where it amplifies the volume and radiance of the whole composition, thereby providing a distinct and most characteristic signature for this modern, elegantly floral feminine fine fragrance composition.

EXAMPLE 8

Woody-Spicy Masculine Perfume Oil for Shower Gels and as After Shave

| COMPOUND/INGREDIENT | PARTS PER WEIGHT 1/900 |
|---|---|
| 1. ALLYL AMYL GLYCOLATE | 2.00 |
| 2. AMBRINOL (2,5,5-TRIMETHYL-1,2,3,4,4A,5,6,7-OCTAHYDRONAPHTHALEN-2-OL) | 0.80 |
| 3. AMBROFIX (DODECAHYDRO-3A,6,6,9A-TETRAMETHYL-NAPHTHOL[2,1-B]FURAN) | 2.00 |
| 4. BOISAMBRENE FORTE ((ETHOXYMETHOXY)CYCLODODECANE) | 15.00 |
| 5. BLACK PEPPER OIL, MADAGASCAR | 10.00 |
| 6. CEPIONATE (METHYL 2-(3'-OXO-2'-PENTYL-CYCLOPENTYL)ACETATE) | 150.00 |
| 7. CETONE V (1-(2,6,6-TRIMETHYLCYCLOHEX-2-EN-1-YL)-HEPTA-1,6-DIEN-3-ONE) | 10.00 |
| 8. CLARY SAGE OIL, FRANCE | 20.00 |
| 9. COSMONE ((5Z)-3-METHYLCYCLOTETRADEC-5-EN-1-ONE) | 11.00 |
| 10. CUMARINE PURE, CRYSTALLINE | 20.00 |
| 11. DIHYDROMYRCENOL | 25.00 |
| 12. DIPROPYLENE GLYCOL (DPG) | 42.47 |
| 13. EVERNYL (METHYL 3,6-DIMETHYLRESORCYLATE) | 1.00 |
| 14. GARDENOL (METHYL PHENYL CARBINYL ACETATE) | 5.00 |
| 15. GEORGYWOOD (2-ACETYL-1,2,3,4,5,6,7,8-OCTAHYDRO-1,2,8,8-TETRAMETHYLNAPHTHALENE) | 55.00 |
| 16. GERANIUM OIL, EGYPT | 10.00 |
| 17. GUAIACWOOD OIL, PARAGUAY | 8.00 |
| 18. (3Z)-HEX-3-ENOL | 1.00 |
| 19. HYDROXYCITRONELLAL | 30.00 |
| 20. INDOL PURE | 0.08 |
| 21. ISO E SUPER (1-(2',3',8',8'-TETRAMETHYL-1',2',3',4',5',6',7',8'-OCTAHYDRONAPHTHALEN-2'-YL)ETHANONE) | 120.00 |
| 22. LAVANDER OIL, FRANCE | 2.00 |
| 23. LEMON OIL, ITALY | 130.00 |
| 24. LINALOOL, SYNTHETIC | 55.00 |
| 25. LINALYL ACETATE, SYNTHETIC | 85.00 |
| 26. MYSTIKAL (2-METHYLUNDECANOIC ACID) | 0.10 |
| 27. NIRVANOLIDE ((10Z)-13-METHYLOXACYCLOPENTADEC-10-EN-2-ONE) | 30.00 |
| 28. PATCHOULI OIL FRACTION, INDONESIA | 20.00 |
| 29. PEPPERMINT OIL BLEND | 2.00 |
| 30. PINK PEPPER BERRIES, $CO_2$ EXTRACT | 3.00 |
| 31. STAR-ANISE OIL, CHINA | 1.00 |
| 32. TIMBEROL (1-(2,2,6-TRIMETHYLCYCLOHEXYL)HEXAN-3-OL) | 7.00 |
| 33. TRICYCLAL (2,4-DIMETHYLCYCLOHEX-3-ENE-1-CARBALDEHYDE) | 1.40 |
| 34. VANILLIN | 0.15 |
| 35. (3E,5E)-5-TERT-BUTYLOCTA-3,5-DIEN-2-ONE | 25.00 |
| | TOTAL: 900.00 |

At less than 3%, (3E,5E)-5-tert-butylocta-3,5-dien-2-one (Example 1) brings in much depth, warmth and body into this masculine chypre composition, especially into its top note and its heart chords. It adds elegance, harmony and value to the composition, prevents it from capsizing into a soapy tune, but instead provides a warm, caressing feeling, and much signature and volume in the functional use of the shampoo or after-shave product. The noble orris radiance of the fragrance, especially in the beginning of the evaporation curve, is in fact due only to its content in (3E,5E)-5-tert-butylocta-3,5-dien-2-one, anticipating and enhancing the woody-ambery fond with its central oakmoss-incense accord, and counterbalancing the spicy, peppery-anisic contrasts in the top to middle section of the fragrance, thereby modernizing this classic composition theme.

The invention claimed is:

1. A compound of the formula (I)

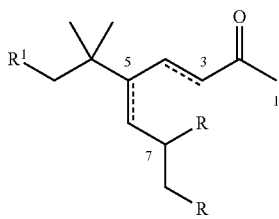

(I)

wherein
R and $R^1$ are independently selected from hydrogen and methyl;
the bond between C-3 and C-4 and the bond between C-5 and C-6 are single bonds; or
the dotted line together with the bond between C-3 and C-4 and the bond between C-5 and C-6 represent double bonds, the compound of formula (I) being characterized by its orris odor.

2. The compound according to claim 1 wherein the dotted line together with the bond between C-3 and C-4 and the bond between C-5 and C-6 represent double bonds, and both double bonds are in (E)-configuration.

3. The compound according to claim 2 selected from (3E,5E)-5-tert-butylocta-3,5-dien-2-one, (3E,5E)-5-(tert-pentyl)octa-3,5-dien-2-one, and (3E,5E)-5-(tert-butyl)-7-methylnona-3,5-dien-2-one.

4. The compound according to claim 1 selected from the group consisting of 5-tert-butylocta-3,5-dien-2-one, 5-(tert-pentyl)octa-3,5-dien-2-one, 5-(tert-butyl)-7-methylnona-3,5-dien-2-one, 5-tert-butyloctan-2-one, 6,6-dimethyl-5-propyloctan-2-one, and 5-tert-butyl-7-methylnonan-2-one.

5. A method of using a compound of formula (I) as a fragrance ingredient, comprising a step of utilizing the compound of formula (I) to form a fragrance

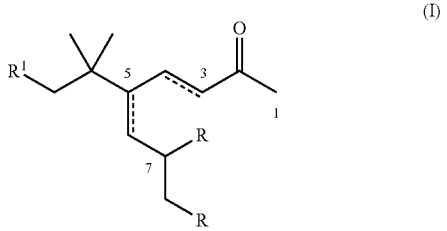

(I)

wherein
R and $R^1$ are independently selected from hydrogen and methyl;
the bond between C-3 and C-4 and the bond between C-5 and C-6 are single bonds; or
the dotted line together with the bond between C-3 and C-4 and the bond between C-5 and C-6 represent double bonds, the compound of formula (I) being characterized by its orris odor.

6. The method according to claim 5, wherein the compound of formula (I) wherein the dotted line together with the bond between C-3 and C-4 and the bond between C-5 and C-6 represent double bonds, and both double bonds are in (E)-configuration.

7. A fragrance composition or a perfumed product comprising a compound of formula (I)

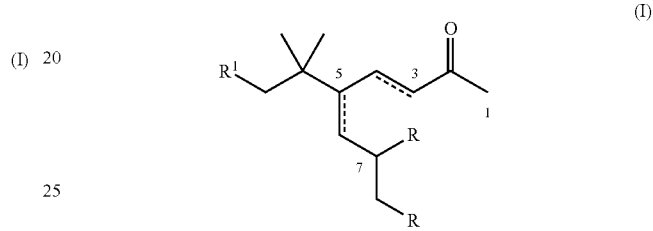

(I)

wherein
R and $R^1$ are independently selected from hydrogen and methyl;
the bond between C-3 and C-4 and the bond between C-5 and C-6 are single bonds; or
the dotted line together with the bond between C-3 and C-4 and the bond between C-5 and C-6 represent double bonds, the compound of formula (I) being characterized by its orris odor.

8. The perfumed product according to claim 7 wherein the product is selected from fine perfumery, fabric care, household products, beauty and personal care products, and air care products.

9. A method of improving, enhancing, or modifying a consumer product base comprising the step of adding thereto an olfactorily acceptable amount of at least one compound of formula (I)

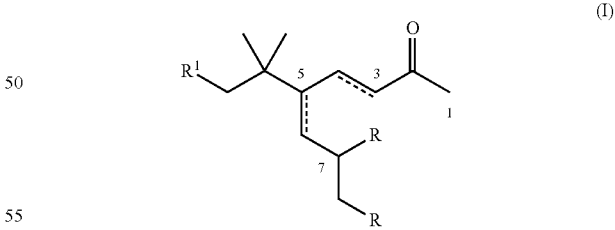

(I)

wherein
R and $R^1$ are independently selected from hydrogen and methyl;
the bond between C-3 and C-4 and the bond between C-5 and C-6 are single bonds; or the dotted line together with the bond between C-3 and C-4 and the bond between C-5 and C-6 represent double bonds,
the at least one compound of formula (I) being characterized by its orris odor.

* * * * *